US008455474B2

(12) United States Patent
Lu et al.

(10) Patent No.: US 8,455,474 B2
(45) Date of Patent: Jun. 4, 2013

(54) METHOD FOR TREATING TUBERCULOSIS

(75) Inventors: Yen-Ta Lu, Taipei (TW); I-Fang Tsai, Taipei (TW)

(73) Assignee: Mackay Memorial Hospital, Zhongshan District, Taipei (TW)

( * ) Notice: Subject to any disclaimer, the term of this patent is extended or adjusted under 35 U.S.C. 154(b) by 219 days.

(21) Appl. No.: 13/041,047

(22) Filed: Mar. 4, 2011

(65) Prior Publication Data
US 2012/0225113 A1    Sep. 6, 2012

(51) Int. Cl.
*A61K 31/397*    (2006.01)
*A61P 31/06*    (2006.01)

(52) U.S. Cl.
USPC .................................... 514/210.02; 548/952

(58) Field of Classification Search
None
See application file for complete search history.

(56) References Cited

U.S. PATENT DOCUMENTS

| 5,631,365 | A |   | 5/1997  | Rosenblum et al. |            |
|-----------|---|---|---------|------------------|------------|
| 5,767,115 | A |   | 6/1998  | Rosenblum et al. |            |
| 5,846,966 | A |   | 12/1998 | Rosenblum et al. |            |
| 5,883,093 | A | * | 3/1999  | Hutchinson et al. | 514/210.02 |

FOREIGN PATENT DOCUMENTS

| WO | 95/08532 A1    | 3/1995 |
|----|----------------|--------|
| WO | 2005/023305 A2 | 3/2005 |
| WO | 2008/039829 A2 | 4/2008 |
| WO | 2008/085300    | 7/2008 |

OTHER PUBLICATIONS

Mehta et al. (2010) 2-Azetidinone—A New Profile of Various Pharmacological Activities, European J. of Medicinal Chemistry 45: 5541-5560.
Galletti & Giacomini (2011) Monocyclic B-Lactams: New Structures for New Biological Activities, Current Medicinal Chemistry 18 (28): 4265-4283.

* cited by examiner

*Primary Examiner* — Sreeni Padmanabhan
*Assistant Examiner* — Irina Neagu
(74) *Attorney, Agent, or Firm* — Thomas Horstemeyer, LLP; Lisa C. Pavento

(57) ABSTRACT

Disclosed is a method for treating a symptom of *M. tuberculosis* infection in a subject, comprising administering the patient with an effective amount of (3R,4S)-1-(4-fluorophenyl)-3-[(3S)-3-(4-fluorophenyl)-3-hydroxypropyl]-4-(4-hydroxyphenyl)zetidin-2-one (EZETIMIBE). In the preferred embodiments, EZETIMIBE is capable of significantly inhibiting the survival and proliferation of *Mycobacterium tuberculosis* in the monocytes. The anti-tuberculous effect of EZETIMIBE is partly through stimulating CD13 leading to monocytes activation and thus bacterial killing of *Mycobacterium tuberculosis*, and partly through depleting the intracellular nutrition necessary for the survival of *Mycobacterium tuberculosis*. It is also proved that EZETIMIBE is capable of directly killing *Mycobacterium tuberculosis* outside cells.

8 Claims, 8 Drawing Sheets

(A)

(B)

(A)

(B)

(A)

(B)

Post-treatment

METHOD FOR TREATING TUBERCULOSIS

BACKGROUND OF THE INVENTION

1. Field of the Invention

The present invention relates to a method for treating tuberculosis. More particularly, the present invention relates a method of using EZETIMIBE for treating a patient suffering from tuberculosis.

2. The Prior Arts

Tuberculosis (TB) is a common and often deadly infectious disease caused by *Mycobacteria* species, usually *Mycobacterium tuberculosis* in humans. Tuberculosis usually attacks the lungs but can also affect other parts of the body. It is spread through the air, when people who have the disease cough, sneeze, or spit. Most infections in humans result in an asymptomatic, latent infection, and about one in ten latent infections eventually progresses to active disease, which, if left untreated, kills more than 50% of its victims.

The classic symptoms are a chronic cough with blood-tinged sputum, fever, night sweats, and weight loss. Infection of other organs causes a wide range of symptoms. Diagnosis relies on radiology (commonly chest X-rays), a tuberculin skin test, blood tests, as well as microscopic examination and microbiological culture of bodily fluids. Treatment is difficult and requires long courses of multiple antibiotics. Contacts are also screened and treated if necessary. Antibiotic resistance is a growing problem in (extensively) multi-drug-resistant tuberculosis. Prevention relies on screening programs and vaccination, usually with *Bacillus* Calmette-Guérin vaccine.

Despite pulmonary tuberculosis can be controlled by drug treatment, the number of infected population is however increasing. One of the problems is that the reliable diagnostic assays capable of rapidly discriminating the latent infection and thus effective treatment are not readily accessible. Therefore, a heretofore unaddressed need exists in the art to address the aforementioned deficiencies and inadequacies, especially in treating tuberculosis caused by *Mycobacterium tuberculosis*.

Azetidinones have been reported as being useful in lowering cholesterol and/or in inhibiting the formation of cholesterol-containing lesions in mammalian arterial walls. U.S. Pat. No. 5,631,365, U.S. Pat. No. 5,767,115 and U.S. Pat. No. 5,846,966 disclose hydroxy-substituted azetidinones useful as hypocholesterolemic agents in the treatment and prevention of atherosclerosisas, and the process for preparing hydroxy-substituted azetidinones. In particular, one of the most commonly used compound is (3R,4S)-1-(4-fluorophenyl)-3-[(3S)-3-(4-fluorophenyl)-3-hydroxypropyl]-4-(4-hydroxyphenyl)zetidin-2-one represented as formula (Ia).

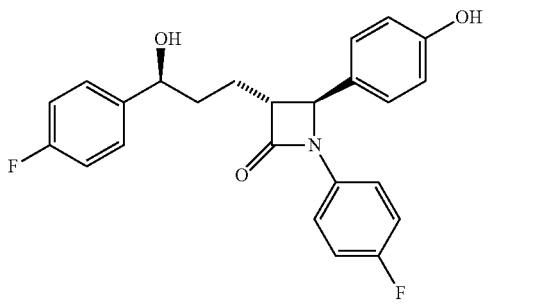

(Ia)

The compound shown as above is (3R,4S)-1-(4-fluorophenyl)-3-[(3S)-3-(4-fluorophenyl)-3-hydroxypropyl]-4-(4-hydroxyphenyl)zetidin-2-one (EZETIMIBE), an anti-hyperlipidemic medication which is used to lower cholesterol levels. It acts by decreasing cholesterol absorption in the intestine. Particularly, EZETIMIBE localizes at the brush border of the small intestine, where it inhibits the absorption of cholesterol from the intestine. Specifically, it appears to bind to a critical mediator of cholesterol absorption, the Niemann-Pick C1-Like 1 (NPC1L1) protein on the gastrointestinal tract epithelial cells as well as in hepatocytes. In addition to this direct effect, decreased cholesterol absorption leads to an upregulation of LDL-receptors on the surface of cells and an increased LDL-cholesterol uptake into cells, thus decreasing levels of LDL in the blood plasma which contribute to atherosclerosis and cardiovascular events. It may be used alone, marketed as Zetia or Ezetrol, when other cholesterol-lowering medications are not tolerated, or together with Statins. However, EZETIMIBE and its related pharmaceutical composition have never been reported to be used for treating tuberculosis.

SUMMARY OF THE INVENTION

It is advantageous to develop a method for treating a patient suffering from tuberculosis.

Therefore, the objective of the present invention is to provide a method using EZETIMIBE or a pharmaceutically acceptable salt thereof for treating a symptom of *Mycobacterium tuberculosis* infection in a subject.

In one aspect, the present invention relates to a method for treating a symptom of *Mycobacterium tuberculosis* infection in a subject, comprising administering the subject an therapeutically effective amount of a compound of structural formula I or the pharmaceutically acceptable salt thereof, wherein

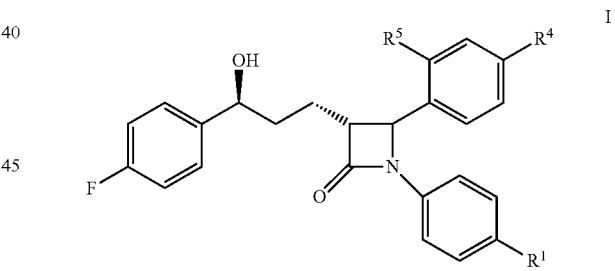

I $R^1$ is selected from the group consisting of chloro, fluoro, —C≡C—$C_{1-6}$alkyl-$NR^2R^3$, —$(CH_2)_X$CH═CH—$C_{1-6}$alkyl-$NR^2R^3$, —$C_{1-8}$alkyl-$NR^2R^3$, —C≡C—$C_{1-4}$alkyl-CH—$(CH_2$—$NR^2R^3)_2$, —$(CH_2)_X$(CH═CH—$C_{1-4}$alkyl-CH—$(CH_2$—$NR^2R^3)_2$, —$C_{1-6}$alkyl-CH—$(CH_2$—$NR^2R^3)_2$, —C≡C—$C_{1-6}$alkyl-$R^{3a}$, —$(CH_2)_X$CH═CH—$C_{1-6}$alkyl-$R^{3a}$, —$C_{1-8}$alkyl-$R^{3a}$—C≡C—$C_{1-6}$alkyl, —$(CH_2)_X$CH═CH—$C_{1-6}$alkyl, —$C_{1-8}$alkyl, —$C_{2-15}$alkynyl mono- or poly-substituted with —OH and optionally substituted with $R^6$, —$C_{2-15}$alkenyl mono- or poly-substituted with —OH and optionally substituted with $R^6$, —$C_{1-15}$alkyl mono- or poly-substituted with —OH and optionally substituted with $R^6$, and x is an integer selected from 0, 1 and 2; $R^2$ is independently selected at each occurrence from the group consisting of —H and —$C_{1-3}$alkyl; $R^3$ is independently selected at each occurrence from the group consisting of —H, —$C_{1-3}$alkyl, —C(O)—$C_{1-3}$alkyl, —C(O)—$NR^2R^2$, —SO$_2$—C$_{1-3}$alkyl and —SO$_2$-phenyl; R$^{3a}$ is selected from the group consisting of —C(O)—NR$^2$R$^2$, —SO$_2$—C$_{1-3}$alkyl, and —SO$_2$-phenyl; R$^4$ is selected from the group consisting of —H, —OH, —C$_{2-15}$alkynyl mono- or poly-substituted with —OH and optionally substituted with R$^6$, —C$_{2-15}$alkenyl mono- or poly-substituted with —OH and optionally substituted with R$^6$, —C$_{1-15}$alkyl mono- or poly-substituted with —OH and optionally substituted with R$^6$; R$^5$ is selected from the group consisting of —H and —OH; and R$^6$ is a sugar residue optionally substituted with —COOH, —COOC$_{1-3}$alkyl and —C$_{1-3}$alkyl-OH.

In another aspect, the present invention relates to a method for preventing a symptom of *Mycobacterium tuberculosis* infection in a subject, comprising administering the patient with a prophylactically effective amount of pharmaceutically acceptable salt of compound or pharmaceutically acceptable salts thereof as above.

In another aspect, the present invention relates to a pharmaceutical composition for treating or preventing a symptom of *Mycobacterium tuberculosis* infection in a subject, comprising the compound as above and a pharmaceutically acceptable carrier, diluent or excipient.

Though EZETIMIBE is an approved drug used in lowering blood lipid level, the following embodiments provide convincible data to prove that EZETIMIBE is capable of significantly inhibiting the survival and proliferation of *Mycobacterium tuberculosis* in the monocytes. The anti-tuberculous effect of EZETIMIBE is partly through stimulating CD13 leading to monocytes activation and thus bacterial killing of *Mycobacterium tuberculosis*, and partly through depleting the intracellular nutrition necessary for the survival of *Mycobacterium tuberculosis*. In addition, the embodiments of the present invention also prove that EZETIMIBE is capable of directly killing *Mycobacterium tuberculosis* outside cells, possibly because EZETIMIBE is in itself an anti-tuberculous antibiotic. Based on these results, a method for treating a patient suffering from tuberculosis using EZETIMIBE is thus established.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The related drawings in connection with the detailed description of the present invention to be made later are described briefly as follows, in which.

DETAILED DESCRIPTION OF THE INVENTION

Figure 1:
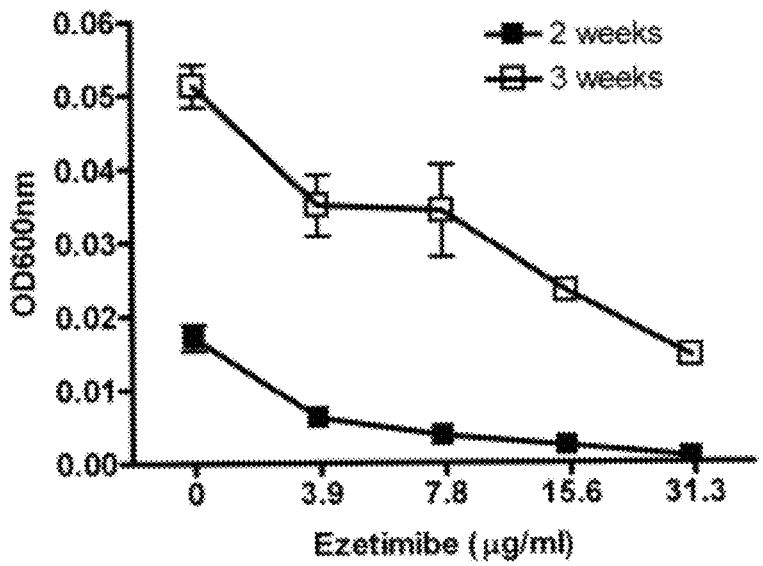
FIGS. 1A-1C show the results of the survival of *Mycobacterium tuberculosis* following exposure to increasing concentrations of EZETIMIBE.
Figure 1:
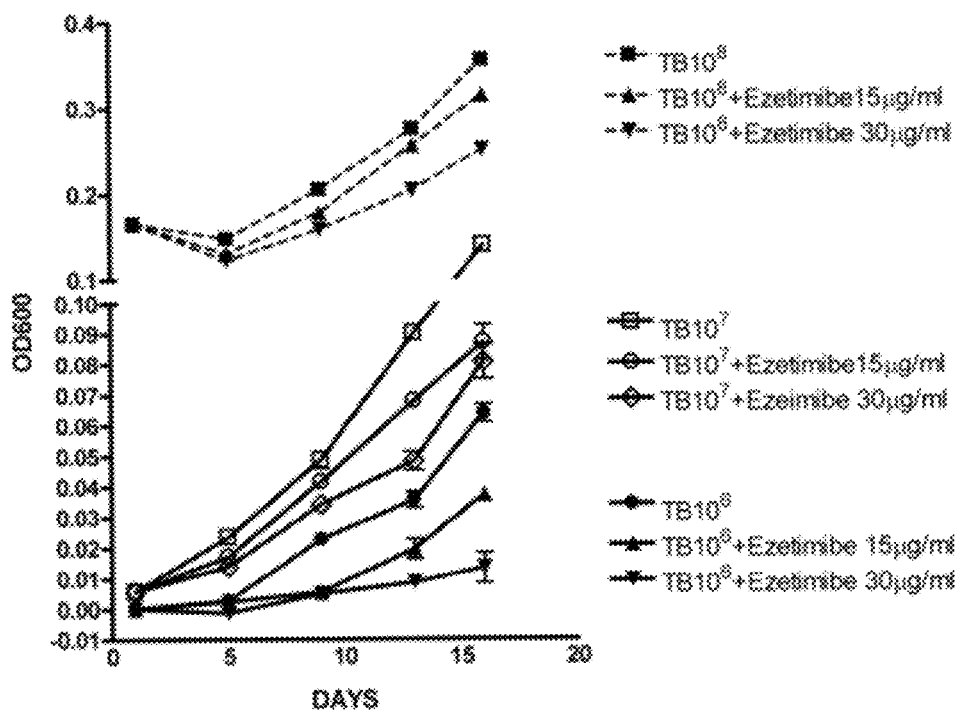
Figure 1:
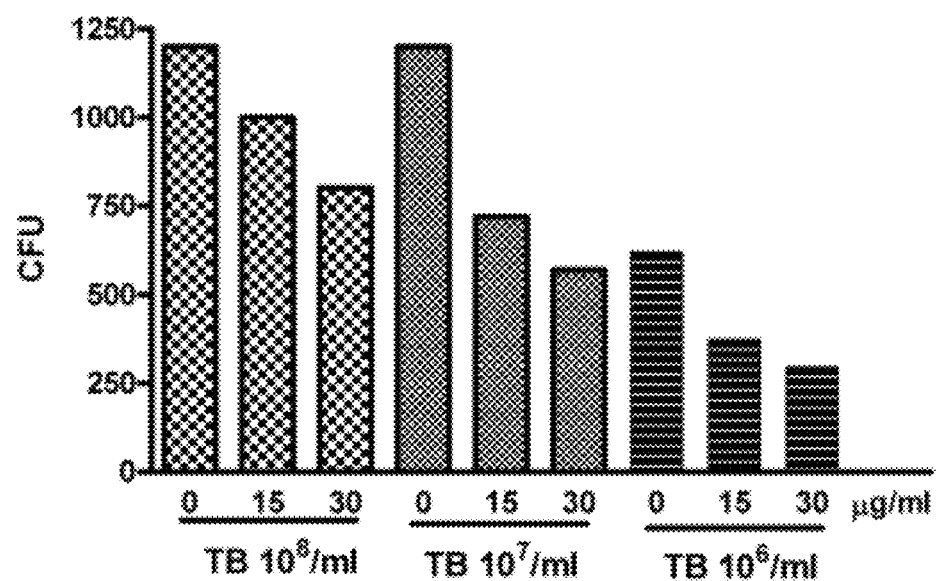
Figure 2:
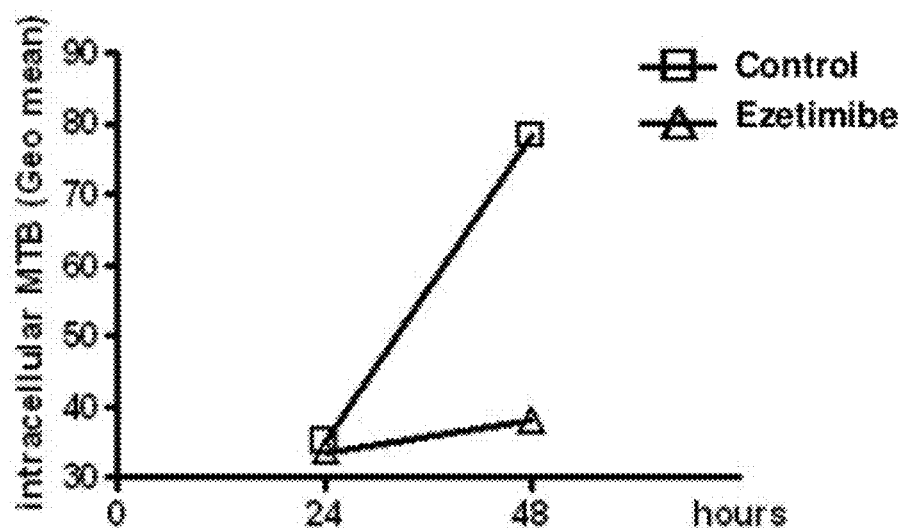
FIGS. 2A-2D show the results pre/post-treatment of EZETIMIBE affects *M. tuberculosis* internalization into monocytes.
Figure 2:
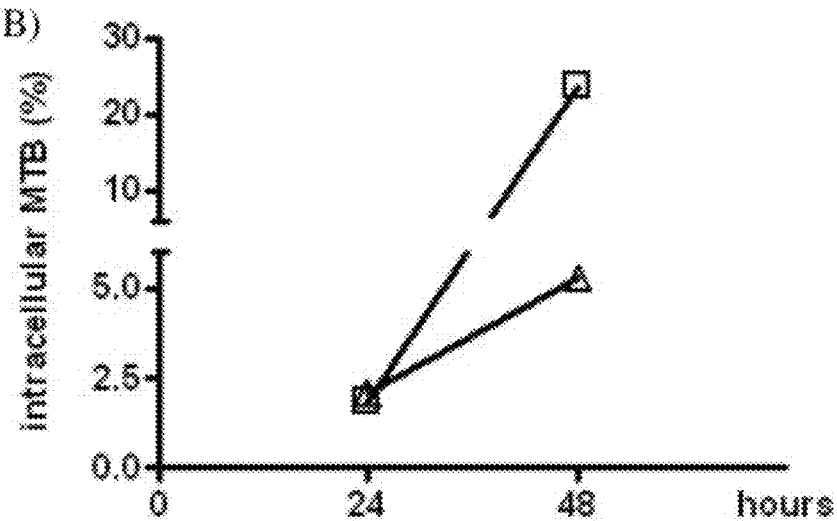
Figure 2:
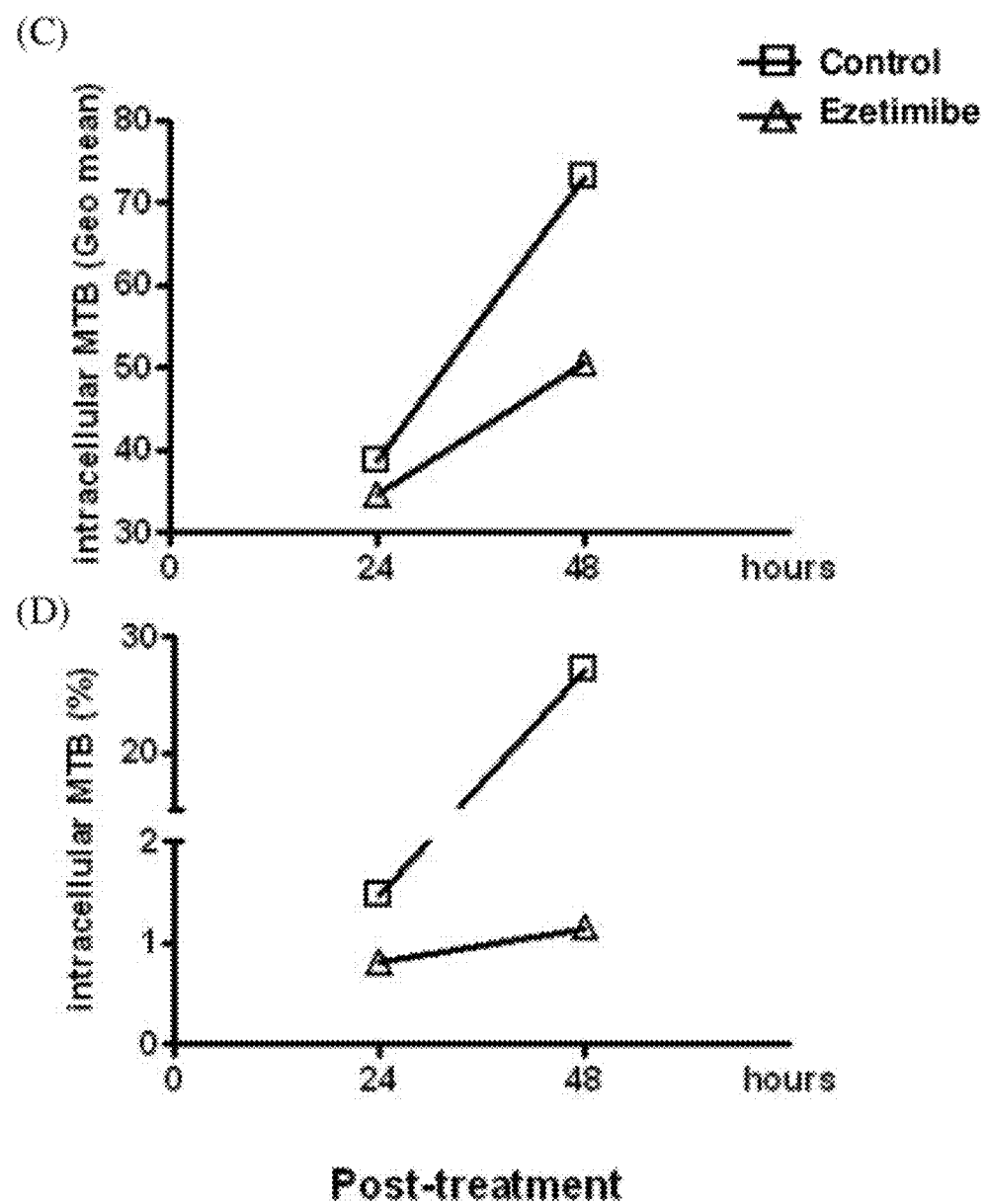
Figure 3:
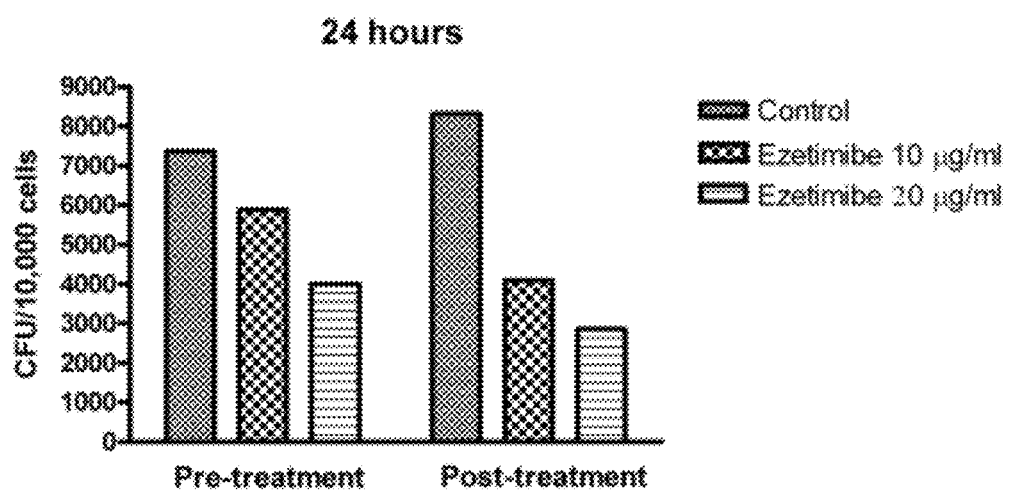
FIG. 3 shows the CFU assay to determine whether treatment with EZETIMIBE affects the intracellular MTB survival and growth.

Before describing in detail embodiments that are in accordance with the present invention, it should be observed that the embodiments reside primarily in combinations of method steps and apparatus components related to method and apparatus for using EZETIMIBE or a pharmaceutically acceptable salt thereof to treat patients suffering from tuberculosis.

The following is a practical example of experiments done relating to the present invention.

Materials and Methods

*Mycobacterium tuberculosis* Preparation

*Mycobacterium tuberculosis* strains were obtained from the culture collection of the Mycobacteriology Laboratory, Mackay Memorial Hospital, Taipei, Taiwan. The organisms were cultured on Lowenstein-Jensen medium slant at 37° C. in a 10% CO$_2$ humidified atmosphere. In mid-log phase, the colonies were harvested and resuspended with PBS. The turbidity of suspension was adjusted to a McFarland 0.5 standard, containing approximately 1×10$^8$ bacteria/ml.

EZETIMIBE Preparation

EZETIMIBE tablets (EZETROL, MSD Schering-Plough) were resolved in acetone and the inactive ingredients were removed by centrifuging at 13000 g for 5 minutes at 25° C. The supernatant contained EZETIMIBE was transferred into a sterile eppendorff and the acetone was evaporated by air-dried for 24 hours. The stock was resolved in ethanol and stored at −20° C.

Killing Kinetics In Vitro

Strains were grown in 7H9 medium and the turbidity of suspension was adjusted to a McFarland 0.5 standard and used as inocula after ten-fold dilution in 7H9 medium with or without various concentrations of EZETIMIBE. The kinetics of bactericidal effect of EZETIMIBE was estimated by measuring the optical density at 600 nm at the indicated time points, followed by plating for colony formation unit (CFU) enumeration on 7H11 agar plates.

Cells and Cell Culture

Peripheral blood mononuclear cells were isolated from whole blood by means of Ficoll-Paque gradient centrifugation. Monocytes were incubated with CD14 microbeads, after which the CD14-positive cells were separated out by a magnet. These cells were seeded in U-bottom 96-well plates at a density of 2×10$^5$ cells in a volume of 200 μl of PRMI-1640 medium with 10% FCS and cultured for 1 hour in the presence or absence of EZETIMIBE (resolved in alcohol). Next, 5×10$^5$ *M. tuberculosis* bacteria were added to each well, followed by incubation for 24 hours. Cell viability was tested by using trypan blue staining. In the post-treatment experiment, monocytes were infected with *M. tuberculosis* bacteria for 1 hour and then added with EZETIMIBE for another 24 hours. In the cholesterol supplement experiment, water soluble cholesterol (Sigma) was resolved in sterile deionized water and added into the culture medium with or without EZETIMIBE.

Flow Cytometry

Infected monocytes described above receiving either EZETIMIBE or control were washed with PBS to remove unbound bacteria and fixed with 4% formalin for 24 hours at 4° C. Then cells were permeabilized by using permeabilization buffer and stained with fluorescein isothiocyanate-conjugated anti-*M. tuberculosis* antibody for 1 hour at 4° C. The fluorescence intensity of intracellular *M. tuberculosis* was than analyzed by flow cytometry. Stained cells were evaluated by FACS Calibur flow cytometer (BD Bioscience). Analysis was performed using CellQuest software (BD Bioscience).

CFU Counts

As time point mentioned, monocytes were harvested and washed three times with PBS. A portion of the cells were treated with trypan blue to assess viability and count cell number. Another portion was lysed by adding 100 µl 0.1% sodium dodecyl sulfate in $H_2O$ and vortexing for 10 minutes. For 10 minutes incubation, 900 µl $H_2O$ was added and the solution was centrifuged at 3400 g for 15 minutes at 4° C. The lysate pellet was washed twice with PBS, after which 50 µl aliquots of lysate in PBS were plated on Lowenstein-Jensen medium and 7H11 agar. The plates were incubated at 37° C. in a 10% $CO_2$ incubator for 3 weeks. The results were reported as mean colony forming units (CFU) per 10,000 monocytes.

Nile Red Staining

A stock solution of nile red (1 mg/ml) in acetone was prepared and stored at 4° C. and protected from light. The nile red solution was added to the cell preparation (final concentration: 1 µg/ml) for 10 minutes and excess dye was washed away with PBS. Nile red fluorescence was examined at two spectral settings, yellow-gold fluorescence (FL1 channel, excitation, 488 nm; emission, 530±30 nm) for cytoplasmic neutral lipids and red fluorescence (FL2 channel, excitation, 488 nm; emission, 585±21 nm) for polar lipids, consist of phospholipids, other amphipathic lipids, and strongly hydrophobic proteins of cell membranes as reported. Stained cells were evaluated by FACS Calibur flow cytometer (BD Bioscience). Analysis was performed using CellQuest software (BD Bioscience).

Statistical Analysis

Distributions of continuous variables were tested for normality using the Kolmogorov-Smirnov test. Variables passed normality test were analyzed using unpaired t test and variables with distributions differing significantly were analyzed using Mann Whitney test, and the values were reported as the mean±SEM. All statistical analyses were performed using Prism 3.0 software (GraphPad Software Inc., San Diego, Calif.). Two-sided tests were used, and P<0.05 was considered statistically significant.

EXAMPLES

The methods and materials of following embodiments were performed according to the contents as previously described.

Example 1

The Effect of EZETIMIBE on the Survival of Mycobacterium tuberculosis

As shown in FIG. 1A, inhibition effect on growth of Mycobacterium tuberculosis in 7H9 broth was found at $2^{nd}$ and $3^{rd}$ week following exposure to increasing concentrations of EZETIMIBE. Also, the effect of EZETIMIBE inhibition on *M. tuberculosis* survival was found in suspension with increasing amount of bacteria (FIG. 1B). Treatment of EZETIMIBE (15 and 30 μg/ml) for 72 hours significantly reduced the colony-forming units (CFU) of *Mycobacterium tuberculosis* on 7H11 agar plate at $3^{rd}$ week (FIG. 1C).

Example 2

The Effect of EZETIMIBE on Internalization of *Mycobacterium tuberculosis* by Monocytes As shown in FIGS. 2A-2D, the experiments were performed to assess whether the treatment of EZETIMIBE affected *M. tuberculosis* internalization into monocytes, and the monocytes were pretreated with EZETIMIBE for 24 hours or 48 hours. According to the results, pre-treatment of monocytes with EZETIMIBE lead to the entry reduction of *M. tuberculosis* into monocytes up to 18.28% in 48 hours. Post-treatment of monocytes with EZETIMIBE lead to the entry reduction of *M. tuberculosis* into monocytes up to 0.65% and 26.02% in 24 hours and 48 hours, respectively.

Example 3

The Effect of EZETIMIBE on Intracellular Survival of *Mycobacterium tuberculosis*

As shown in FIG. 3, the CFU assays were performed to determine whether treatment with EZETIMIBE affect the intracellular *M. tuberculosis* survival and growth. In the pre-treatment experiment, monocytes were treated with EZETIMIBE for 1 hour and then infected with *M. tuberculosis* bacteria for another 24 hours. Treatment with 10 ng/ml and 20 ng/ml (resolved in alcohol) of EZETIMIBE reduced the CFU counts from 7358 to 5880 and 4000 per 10,000 cells, respectively. In the post-treatment experiment, monocytes were firstly infected with *M. tuberculosis* bacteria for 1 hour followed by treatment with EZETIMIBE for another 24 hours. Treatment with EZETIMIBE of 10 ng/ml and 20 ng/ml for 24 hours reduced CFU counts from 8320 to 4090 and 2858 per 10,000 cells, respectively.

As data shown, whether for pre-treatment or post-treatment, it is suggested that EZETIMIBE was capable of effectively lowering intracellular survival of *M. tuberculosis.*

Example 4

The Effect of EZETIMIBE on CD13 Expression on Monocytes

As shown in FIG. 4, the experiments were performed to assess whether the treatment of EZETIMIBE affected CD13 expression on monocytes, and the monocytes were pretreated with EZETIMIBE for 24 hours or 48 hours and were stained by antiCD13 antibodies (clone WM15 and WM47). According to the results, whether pre-treatment of monocytes with EZETIMIBE lead to the down-regulation of CD13 expression on monocytes.

As data shown, EZETIMIBE was capable of effectively lowering CD13 expression on monocytes and CD13 can be the target of EZETIMIBE.

Example 5

EZETIMIBE Reduces the Cholesterol Uptake of Monocytes Whether Infection of *M. tuberculosis* or Not As shown in FIGS. 5A-B, monocytes were infected with *M. tuberculosis* bacteria followed by treatment with EZETIMIBE for 24 hours. Nile red staining was used to assess the intracellular lipid droplets by flow cytometry. Nile red fluorescence was examined at two spectral settings, yellow-gold fluorescence (FL1 channel, excitation, 488 nm; emission, 530±30 nm) for cytoplasmic neutral lipids, included triglyceride, cholesterol, cholesterol esters and free fatty acid, and red fluorescence (FL2 channel, excitation, 488 nm; emission, 585±21 nm) for polar lipids. Significant increase fluorescence intensity of FL1 channel not FL2 channel was observed following cholesterol supplement (10 μg/ml) in monocytes culture without infection, and EZETIMIBE (10 μg/ml and 20 μg/ml) can inhibit the uptake of cholesterol by reducing the relative fluorescence of FL1 channel from 1.5 to 1.2 and 1.3, respectively. As infection with *M. tuberculosis* with cholesterol supplement (10 μg/ml) for 24 hours, treatment with EZETIMIBE also significantly reduced the relative fluorescence of FL1 channel from 1.4 to 0.9 and 1.0, respectively.

As data shown, EZETIMIBE was capable of effectively lowering cholesterol uptake of monocytes whether infection or not.

Example 6

The Role of Cholesterol in EZETIMIBE Inhibition on Intracellular Survival of *Mycobacterium tuberculosis*

Figure 4:
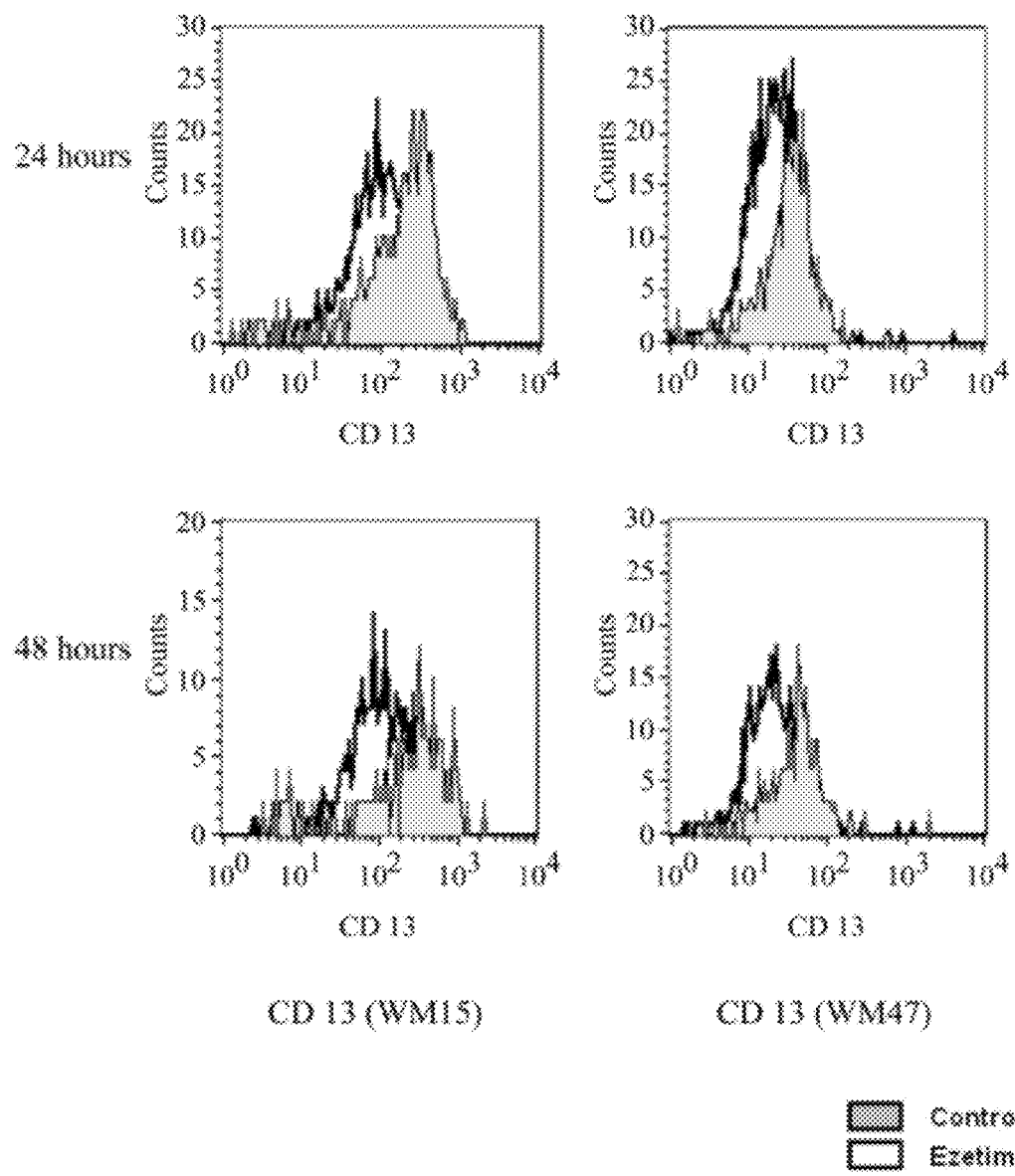
FIG. 4 shows that EZETIMIBE was capable of effectively lowering CD13 expression on monocytes and CD13 can be the target of EZETIMIBE.
Figure 5:
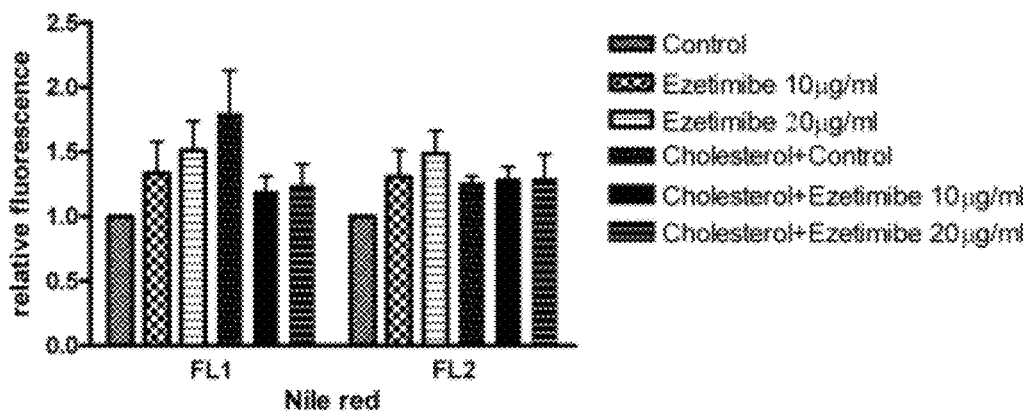
FIGS. 5A-5B display the nile red staining results of monocytes infected with or without *M. tuberculosis* bacteria followed by treatment with/without EZETIMIBE for another 24 hours.
Figure 5:
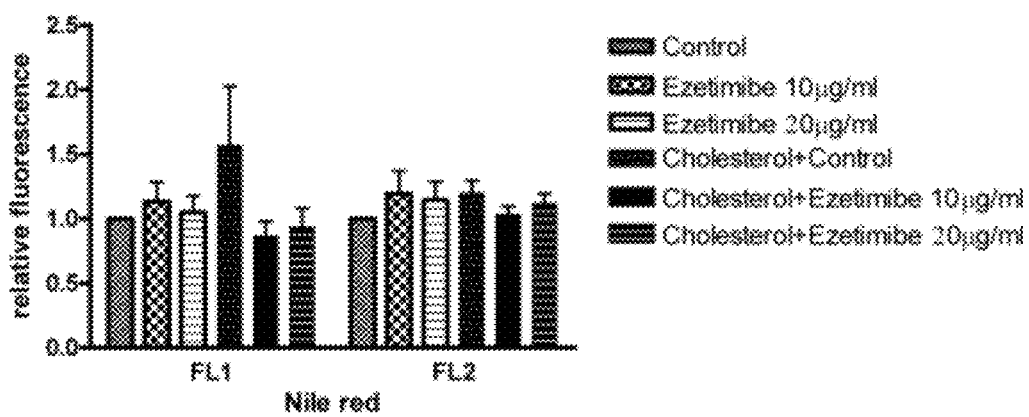
Figure 6:
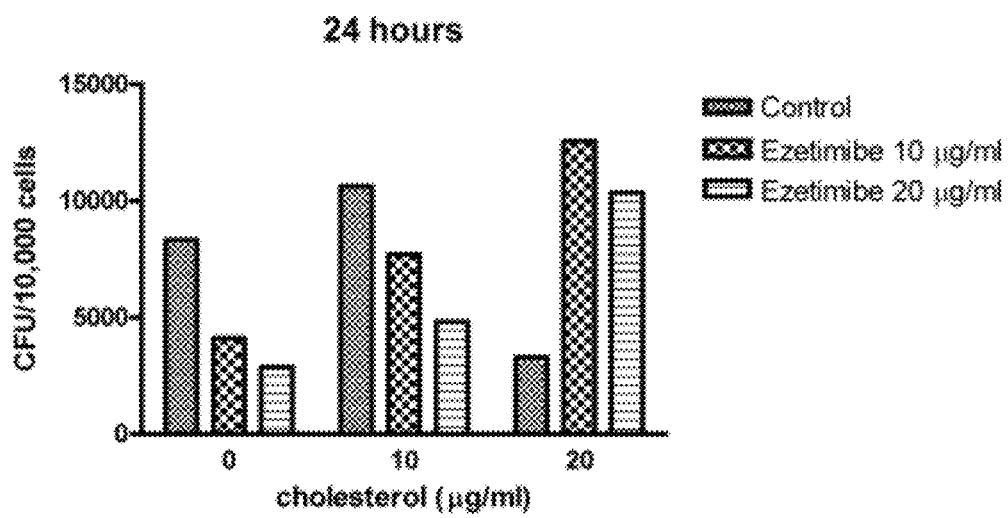
FIGS. 6A-6B show the result of the recovered effect on EZETIMIBE inhibition on intracellular survival of *Mycobacterium tuberculosis* by high dose cholesterol supplement.
Figure 6:
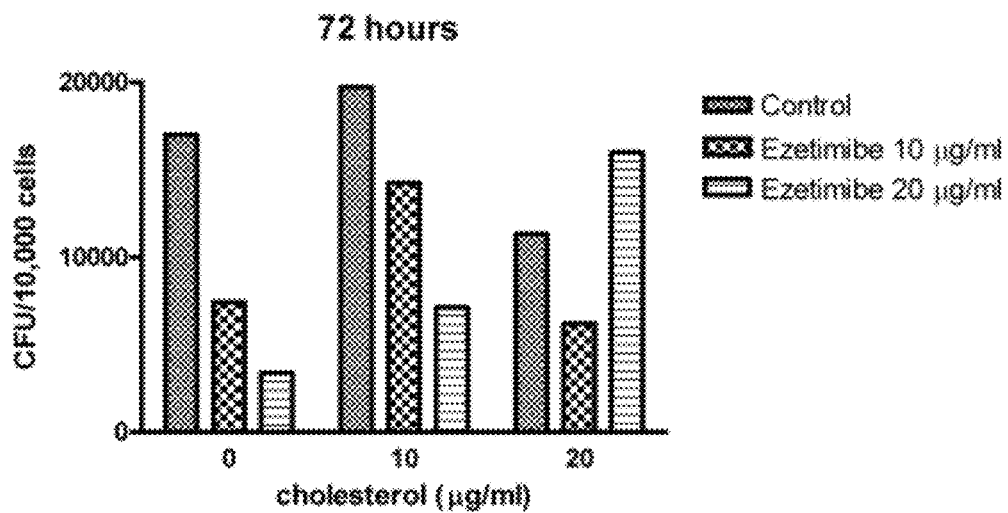

As shown in FIGS. 6A-B, the CFU assays were performed to determine whether treatment with EZETIMIBE following cholesterol supplement affect the intracellular *M. tuberculosis* survival and growth. In the post-treatment experiment, monocytes were firstly infected with *M. tuberculosis* bacteria for 1 hour followed by treatment with EZETIMIBE for another 24 and 72 hours. Treatment with EZETIMIBE of 10 μg/ml and 20 μg/ml following cholesterol supplement (10 μg/ml) for 24 hours reduced CFU counts from 10600 to 7692 and 4800 per 10,000 cells, respectively. However, increase the cholesterol supplement up to 20 μg/ml, the effect of inhibition of bacterial survival by EZETIMIBE 10 μg/ml and 20 μg/ml were recovered and the CFU counts were 12545 and 10333 per 10,000 cells, respectively. Also, the similar result was found in 72-hours treatment (FIG. 4B).

As data shown, it is suggested that inhibition of intracellular *M. tuberculosis* survival and growth by EZETIMIBE can be recovered with addition of high does of cholesterol.

In conclusion, the data suggest that EZETIMIBE significantly contribute to intracellular survival and growth of *Mycobacterium tuberculosis*. The anti-tuberculous effect of EZETIMIBE is partly through stimulating CD13 leading to monocytes activation and thus bacterial killing of *Mycobacterium tuberculosis*, and partly through interfering in the cholesterol uptake and utilizing necessary for the survival of *Mycobacterium tuberculosis*. It is also proved that EZETIMIBE is capable of directly killing *Mycobacterium tuberculosis* outside cells.

In another example, a method for treating a symptom of *Mycobacterium tuberculosis* infection in a subject is also disclosed. The method comprises administering the subject an therapeutically effective amount of a compound of structural formula I or the pharmaceutically acceptable salt thereof, wherein $R^1$ is selected from the group consisting of chloro, fluoro, —C≡C—$C_{1-6}$alkyl-$NR^2R^3$, —$(CH_2)_x$CH=CH—$C_{1-6}$alkyl-$NR^2R^3$, —$C_{1-8}$alkyl-$NR^2R^3$, —C≡C—$C_{1-4}$alkyl-CH—$(CH_2$—$NR^2R^3)_2$, —$(CH_2)_x$(CH=CH—$C_{1-4}$alkyl-CH—$(CH_2$—$NR^2R^3)_2$, —$C_{1-6}$alkyl-CH—$(CH_2$—$NR^2R^3)_2$, —C≡C—$C_{1-6}$alkyl-$R^{3a}$, —$(CH_2)_x$CH=CH—$C_{1-6}$alkyl-$R^{3a}$, —$C_{1-8}$alkyl-$R^{3a}$—C≡C—$C_{1-6}$alkyl, —$(CH_2)_x$CH=CH—$C_{1-6}$alkyl, —$C_{1-8}$alkyl, —$C_{2-15}$alkynyl mono- or poly-substituted with —OH and optionally substituted with $R^6$, —$C_{2-15}$alkenyl mono- or poly-substituted with —OH and optionally substituted with $R^6$, —$C_{1-15}$alkyl mono- or poly-substituted with —OH and optionally substituted with $R^6$, and x is an integer selected from 0, 1 and 2; $R^2$ is independently selected at each occurrence from the group consisting of —H and —$C_{1-3}$alkyl; $R^3$ is independently selected at each occurrence from the group consisting of —H, —$C_{1-3}$alkyl, —C(O)—$C_{1-3}$alkyl, —C(O)—$NR^2R^2$, —$SO_2$—$C_{1-3}$alkyl and —$SO_2$-phenyl; $R^{3a}$ is selected from the group consisting of —C(O)—$NR^2R^2$, —$SO_2$—$C_{1-3}$alkyl, and —$SO_2$-phenyl; $R^4$ is selected from the group consisting of —H, —OH, —$C_{2-15}$ alkynyl mono- or poly-substituted with —OH and optionally substituted with $R^6$, —$C_{2-15}$alkenyl mono- or poly-substituted with —OH and optionally substituted with $R^6$, —$C_{1-15}$ alkyl mono- or poly-substituted with —OH and optionally substituted with $R^6$; $R^5$ is selected from the group consisting of —H and —OH; and $R^6$ is a sugar residue optionally substituted with —COOH, —COO$C_{1-3}$alkyl and —$C_{1-3}$alkyl-OH. Particularly, the subject is a mammal (e.g. human), and the compound or the pharmaceutically acceptable salt thereof is administered orally, parentally, or topically.

Compounds of formula I can be synthesized in accordance with WO Pub. No. 2008/085300 published to Devita, et al. on Jul. 17, 2008, the teachings of which are incorporated herein by reference.

In another example, a method for preventing a symptom of *Mycobacterium tuberculosis* infection in a subject is also disclosed. The method comprises administering the subject a prophylactically effective amount of the compound as above or the pharmaceutically acceptable salt thereof. Similarly, the subject is a mammal (e.g. human), and the compound or the pharmaceutically acceptable salt thereof is administered orally, parentally, or topically.

In another example, a pharmaceutical composition for treating or preventing a symptom of *Mycobacterium tuberculosis* infection in a subject is also disclosed. The composition comprises the compound as above and a pharmaceutically acceptable carrier, diluent or excipient. The pharmaceutical composition is in the form of a tablet, a capsule, a powder, a granule, a solution, an emulsion, a gel, a transdermal patch, an aerosol, a microcapsule, or a liposome. The subject being administered is a mammal (e.g. human).

In the foregoing specification, specific embodiments of the present invention have been described. However, one of the ordinary skill in the art appreciates that various modifications and changes can be made without departing from the scope of the present as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method for treating a *Mycobacterium tuberculosis* infection in a subject in need thereof, comprising administering to the subject a therapeutically effective amount of (3R,4S)-1-(4-fluorophenyl)-3-[(3S)-3-(4-fluorophenyl)-3-hydroxypropyl]-4-(4-hydroxyphenyl)azetidin-2-one or a pharmaceutically acceptable salt thereof.

2. The method as claimed in claim 1, wherein the subject is a mammal.

3. The method as claimed in claim 2, wherein the mammal is a human.

4. The method as claimed in claim 1, wherein the compound or the pharmaceutically acceptable salt thereof is administered orally, parentally, or topically.

5. A method for prophylactically treating a *Mycobacterium tuberculosis* infection in a subject in need thereof, comprising administering to the subject a prophylactically effective amount of the compound as claimed in claim 1 or the pharmaceutically acceptable salt thereof.

6. The method as claimed in claim 5, wherein the subject is a mammal.

7. The method as claimed in claim 6, wherein the mammal is a human.

8. The method as claimed in claim 5, wherein the compound or the pharmaceutically acceptable salt thereof is administered orally, parentally, or topically.

* * * * *